US007815601B2

(12) United States Patent
Jordan et al.

(10) Patent No.: US 7,815,601 B2

(45) Date of Patent: Oct. 19, 2010

(54) RAPID EXCHANGE ENTERAL STENT DELIVERY SYSTEM

(75) Inventors: Gary A. Jordan, Litchfield, NH (US); Gary J. Leanna, Holden, MA (US); George T. Roberts, Lincoln, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 4 days.

(21) Appl. No.: 12/022,337

(22) Filed: Jan. 30, 2008

(65) Prior Publication Data

US 2008/0188804 A1 Aug. 7, 2008

Related U.S. Application Data

(60) Provisional application No. 60/888,189, filed on Feb. 5, 2007.

(51) Int. Cl.
*A61M 31/00* (2006.01)

(52) U.S. Cl. .................................................. 604/103.04

(58) Field of Classification Search ............. 604/103.04
See application file for complete search history.

(56) References Cited

U.S. PATENT DOCUMENTS

| | | | |
|---|---|---|---|
| 4,655,771 | A | 4/1987 | Wallsten |
| 4,848,343 | A | 7/1989 | Wallsten et al. |
| 4,990,151 | A | 2/1991 | Wallsten |
| 5,026,377 | A | 6/1991 | Burton et al. |
| 5,135,535 | A | 8/1992 | Kramer |
| 5,217,482 | A | 6/1993 | Keith |
| 5,324,269 | A | 6/1994 | Miraki |
| 5,360,401 | A | 11/1994 | Turnland |
| 5,370,655 | A | 12/1994 | Burns |
| 5,389,087 | A | 2/1995 | Miraki |
| 5,458,605 | A | 10/1995 | Klemm |
| 5,484,444 | A | 1/1996 | Braunschweiler et al. |
| 5,507,768 | A | 4/1996 | Lau et al. |
| 5,533,968 | A | 7/1996 | Muni et al. |
| 5,643,278 | A | 7/1997 | Wijay |

(Continued)

FOREIGN PATENT DOCUMENTS

| | | |
|---|---|---|
| EP | 0 505 686 B1 | 9/1992 |

(Continued)

OTHER PUBLICATIONS

U.S. Appl. No. 12/337,151 to Gerdts et al., filed Dec. 17, 2008.

*Primary Examiner*—Nicholas D Lucchesi
*Assistant Examiner*—Jason Flick
(74) *Attorney, Agent, or Firm*—Vidas, Arrett & Steinkraus

(57) ABSTRACT

Methods of and devices for palliating gastrointestinal strictures using rapid exchange type enteral stent placement catheters. The catheter may include an inner member and an outer member, with the two members being slidable with respect to one another. In various device embodiments, a ramp for directing a guidewire out from within the catheter is provided using portions of the outer member or a shaped mandrel. The inner member may take a number of forms, including a tubular distal portion, a skived or integrally attached elongate midsection, and a proximal portion. A mandrel can be used in a portion proximal of the guidewire ramp, with the mandrel taking one of several disclosed forms.

10 Claims, 16 Drawing Sheets

U.S. PATENT DOCUMENTS

| | | | | |
|---|---|---|---|---|
| 5,690,644 | A | 11/1997 | Yurek et al. | |
| 5,709,703 | A | 1/1998 | Lukic et al. | |
| 5,743,874 | A | 4/1998 | Fischell et al. | |
| 5,782,855 | A | 7/1998 | Lau et al. | |
| 5,843,028 | A | 12/1998 | Weaver et al. | |
| 5,921,971 | A | 7/1999 | Agro et al. | |
| 5,980,533 | A | 11/1999 | Holman | |
| 6,007,522 | A | 12/1999 | Agro et al. | |
| 6,059,752 | A | 5/2000 | Segal | |
| 6,077,295 | A | 6/2000 | Limon et al. | |
| 6,113,607 | A | 9/2000 | Lau et al. | |
| 6,309,379 | B1 | 10/2001 | Willard et al. | |
| 6,380,457 | B1 | 4/2002 | Yurek et al. | |
| 6,398,799 | B2 | 6/2002 | Kramer | |
| 6,488,694 | B1 | 12/2002 | Lau et al. | |
| 6,527,789 | B1 | 3/2003 | Lau et al. | |
| 6,582,459 | B1 | 6/2003 | Lau et al. | |
| 6,592,549 | B2 * | 7/2003 | Gerdts et al. | 604/103.04 |
| 6,723,071 | B2 | 4/2004 | Gerdts et al. | |
| 6,764,484 | B2 | 7/2004 | Richardson et al. | |
| 6,890,317 | B2 | 5/2005 | Gerdts et al. | |
| 7,001,358 | B2 | 2/2006 | Fitzmaurice et al. | |
| 7,115,109 | B2 | 10/2006 | Gerdts et al. | |
| 7,468,053 | B2 | 12/2008 | Gerdts et al. | |
| 2001/0007082 | A1 | 7/2001 | Dusbabek et al. | |
| 2002/0013599 | A1 | 1/2002 | Limon et al. | |
| 2003/0093106 | A1 | 5/2003 | Brady et al. | |
| 2003/0109886 | A1 | 6/2003 | Keegan et al. | |
| 2004/0082935 | A1 * | 4/2004 | Lee et al. | 604/523 |
| 2004/0133263 | A1 | 7/2004 | Dusbabek et al. | |
| 2007/0142821 | A1 * | 6/2007 | Hennessy et al. | 604/528 |

FOREIGN PATENT DOCUMENTS

| | | | |
|---|---|---|---|
| JP | 7-47133 | A | 2/1995 |
| WO | 94/15549 | A1 | 7/1994 |
| WO | 99/49808 | A1 | 10/1999 |
| WO | 00/69498 | A1 | 11/2000 |
| WO | 02/74378 | A2 | 9/2002 |
| WO | 03/002033 | A1 | 1/2003 |

* cited by examiner 140
42
146
160
170
172

120
129
132
134
44
46
126
136
138
48
5A
5B
128

126
130

128
126

20

RAPID EXCHANGE ENTERAL STENT DELIVERY SYSTEM

REFERENCE TO RELATED APPLICATIONS

This application claims the benefit of U.S. Provisional Application Ser. No. 60/888,189, filed Feb. 5, 2007, the entire disclosure of which is incorporated herein by reference.

This application is related to U.S. patent application Ser. No. 11/525,269, filed Sep. 22, 2006; which is a continuation of co-pending U.S. application Ser. No. 11/094,401, filed Mar. 30, 2005; which is a continuation of U.S. application Ser. No. 10/785,350, filed Feb. 24, 2004, now U.S. Pat. No. 6,890,317; which is a continuation of U.S. application Ser. No. 10/454,269, filed Jun. 4, 2003, now U.S. Pat. No. 6,723, 071; which is a continuation of U.S. application Ser. No. 09/808,626, filed Mar. 14, 2001, now U.S. Pat. No. 6,592, 549; the entire disclosures of which are all incorporated herein by reference.

FIELD

The present invention is related to the fields of medical devices and medical procedures. More particularly, the present invention is related to devices and methods for treatment of enteral obstructions such as a stent and a stent delivery system.

BACKGROUND

Endoscopic procedures for treating abnormal pathologies within the alimentary canal system and biliary tree (including the biliary, hepatic, and pancreatic ducts) are increasing in number. The endoscope provides access to the general area of a desired duct using direct visualization. However, the duct itself must be navigated using a catheter in conjunction with a guidewire under fluoroscopy. A wide variety of catheters are known for treatment of such targeted anatomical regions. Examples of biliary catheters are disclosed in U.S. Pat. No. 5,921,971 to Agro et al. and PCT International Publication No. 00/69498 to De Toledo et al., the disclosures of which are hereby incorporated by reference.

Agro et al. disclose a catheter for use in biliary procedures, wherein the catheter includes a shaft having a proximal end and a distal end. A guidewire lumen extends through the shaft from a proximal guidewire port located proximal of the distal end of the shaft, to a distal guidewire port located at the distal end of the shaft. The shaft may also include a slot or channel extending from a proximal end of the shaft to the proximal guidewire port. Catheters incorporating such a guidewire opening and channel are often referred to as rapid exchange or single-operator-exchange type biliary catheters.

De Toledo et al. disclose a single operator drainage catheter delivery system including a guide member having a guidewire lumen extending through a distal portion thereof, with a proximal guidewire port located distal of the proximal end. A placement catheter disposed over the guide member has a catheter lumen extending through a distal portion thereof, with a proximal guidewire port located distal of the proximal end. Locating the proximal guidewire ports as such allows the delivery system to be used by a single person with a shorter guidewire. A drainage catheter (a.k.a. a plastic stent) is disposed about the guide member distal of the placement catheter. The drainage catheter delivery system preferably includes a means for releasably connecting the placement catheter to the drainage catheter, wherein the releasable connecting means disconnects the drainage catheter upon displacement of the guide member. However, De Toledo et al. '498 does not disclose a rapid exchange biliary catheter system for the delivery of a metallic self-expanding stent, which requires a retractable sheath.

U.S. Pat. No. 5,484,444 to Braunschweiler et al., and U.S. Pat. No. 5,709,703 to Lukic et al. disclose a stent delivery device which has an elongated sheath with a self-expandable stent placed in contracted condition within the distal area of the sheath. An elongated core is arranged in the sheath for longitudinal motion relative to the sheath to facilitate stent delivery. However, Braunschweiler et al. '444 and Lukic et al. '703 do not provide a rapid exchange feature as in De Toledo et al. '498.

U.S. Pat. No. 5,743,874 to Fischell et al. discloses a catheter capable of performing balloon angioplasty followed by delivery of a self-expanding stent. The catheter includes an outer sheath which may be pulled back to deploy the self-expanding stent. In one embodiment, the catheter includes a guide wire entry port located just proximal of the stent to permit rapid exchange capability. To provide the guide wire entry port, Fischell et al. '874 provides a sloped plug disposed in the inner tube and an elongate side opening in the outer sheath. The elongate side opening in the outer sheath is necessary to permit retraction of the outer sheath for stent deployment. By providing such a long side opening, a major portion of the inner workings of the catheter are exposed to bodily fluids and interference from other devices, which may compromise performance of the stent delivery catheter. This undesirable feature, in addition to others not specifically mentioned herein, leaves a need for an improved rapid exchange stent delivery catheter.

Gastrointestinal strictures in the duodenum and intestines are known to occur for a variety of reasons, often due to impingement or compression caused by an adjacent tumor. A stent may be placed in an enteral region in order to palliate a gastrointestinal structure, keeping a location from being blocked and allowing a patient to have a more normal diet and lifestyle than would otherwise be possible. For example, a stent may be placed by advancing a guidewire and ERCP catheter through an endoscope working channel into an enteral region for the purpose of contrast infusion. The ERCP catheter can then be withdrawn, and a catheter loaded with a self-expanding stent can be advanced over the guidewire to or near an identified stricture. The stent is then released and self-expands to open the stricture. However, enteral stenting has been performed using over-the-wire devices only.

SUMMARY

The present invention, in an illustrative embodiment, includes a method of palliating a gastrointestinal stricture using a rapid exchange type of enteral stent placement catheter. The catheter may include an inner member and an outer member, with the two members being slidable with respect to one another. The outer member includes a ramp that extends down into a guidewire channel in the inner member. The ramp may be slidable within the guidewire channel as well. The ramp is placed near the distal end of the catheter such that a guidewire need only traverse a distal section of the inner member. Nearer the distal end of the catheter, a self-expanding stent is placed between the inner member and the outer member when the outer member is in a first position. By creating relative movement between the inner member and the outer member, the stent may be released by causing the outer member to no longer cover the self-expanding stent. Once released, the stent self-expands to at least partially unblock the stricture.

In another embodiment, a rapid exchange catheter for deployment of a self-expanding stent includes an outer member having a distal tubular restraining section as well as a guidewire port, and an inner member having a distal portion adapted to carry a self-expanding stent within the restraining section. A mandrel is provided within the outer member, the mandrel coupled with the outer member to preserve axial alignment of the distal end of the mandrel with the guidewire port. The distal end of the mandrel is shaped to form a ramp for allowing a guidewire to smoothly pass from within the outer tubular member out through the guidewire port to the outside of the catheter.

The present invention further includes devices adapted for use as rapid exchange type stent placement catheters. In a first illustrative embodiment, a rapid exchange type catheter for use with a self-expanding stent includes an outer tubular member, an inner member, and a mandrel. In the illustrative embodiment, the inner member includes a distal tubular member coupled to the distal end of a proximal elongate member. For the illustrative embodiment, the outer tubular member includes a guidewire opening. The mandrel may be sized or shaped to fit next to the proximal elongate member within the outer tubular member, and terminates near the proximal end of the guidewire opening of the outer tubular member. In several further embodiments, the proximal elongate member takes the form of a push wire or other solid member that connects to the distal tubular member.

DETAILED DESCRIPTION

The following detailed description should be read with reference to the drawings. The drawings, which are not necessarily to scale, depict illustrative embodiments and are not intended to limit the scope of the invention. Those skilled in the art will recognize that the dimensions and materials discussed herein are merely exemplary and are not intended to limit the scope of the present invention, which is, of course, defined by the appended claims.

As used herein, the term pushwire is not intended to indicate that a catheter is steerable. Instead, the pushwire is used to transmit a pushing force to a distal part of a catheter. For several embodiments, a pushwire is used to transmit a pushing force (typically in conjunction with a corresponding pulling force) that causes a self-expanding stent carried by a first tubular member and constrained by a second tubular member to be expelled from the second tubular member and deployed at a desired location.

Figure 1:
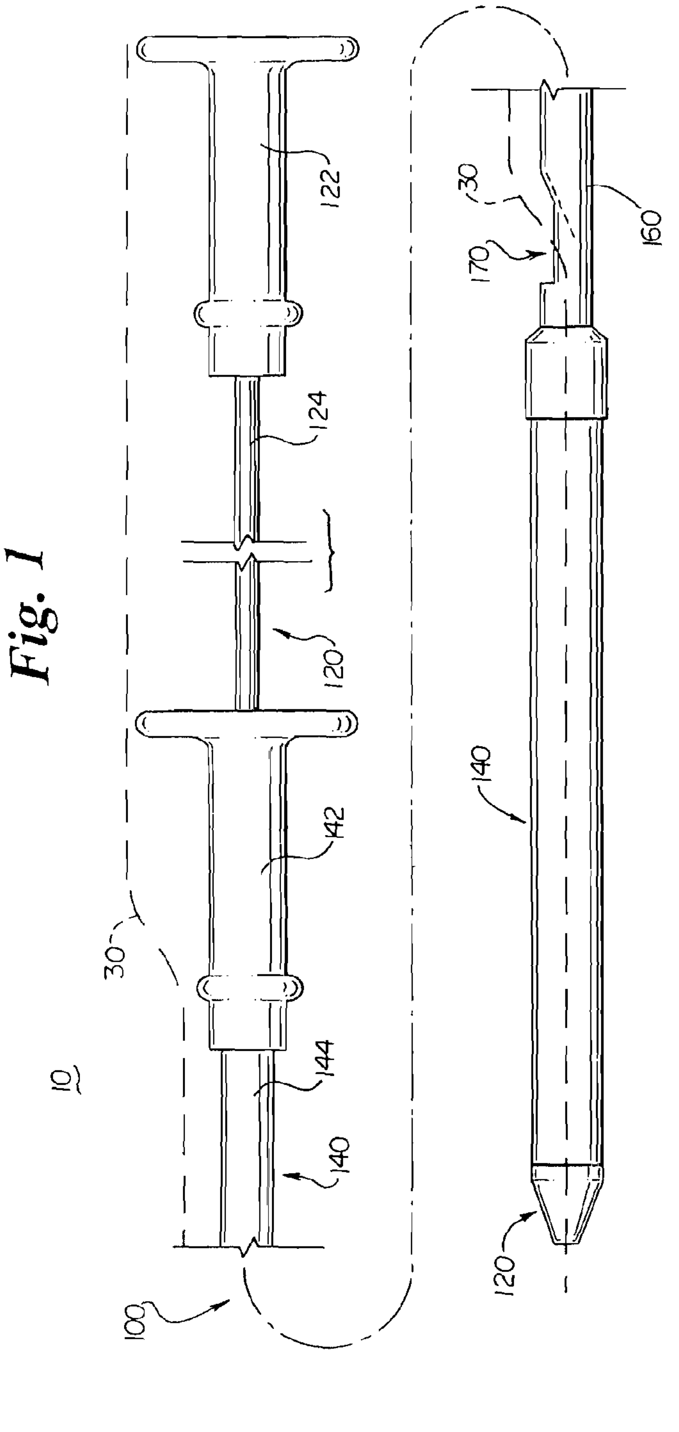
FIG. 1 is a plan view of a rapid exchange stent delivery catheter system in accordance with an illustrative embodiment of the present invention, shown in the delivery state.
Figure 2:
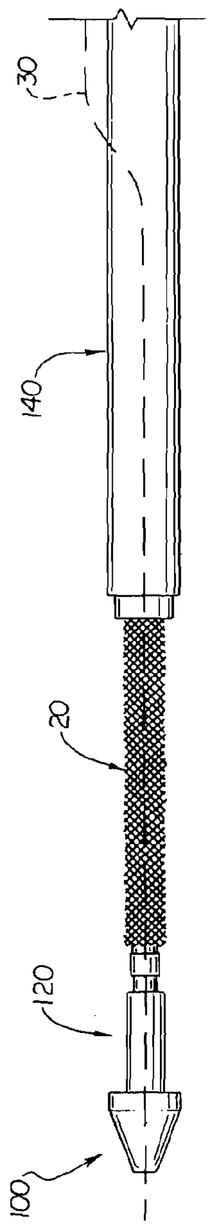
FIG. 2 is a plan view of a distal portion of the rapid exchange stent delivery catheter system illustrated in FIG. 1, shown in the deployment state.

Refer now to FIGS. 1 and 2, which illustrate plan views of a rapid exchange stent delivery catheter system 10 in accordance with an embodiment of the present invention. The rapid exchange stent delivery catheter system 10 includes a rapid exchange catheter 100 which is advanced over a guidewire 30 (shown in phantom) to deliver and deploy a self-expanding stent 20 in a bodily lumen.

The rapid exchange stent delivery catheter system 10 is suitable for biliary and/or gastrointestinal applications. In biliary applications, the rapid exchange stent delivery catheter system 10 is sized to fit within an endoscope (not shown) and to navigate to the desired site in the biliary tract. In vascular applications, the rapid exchange stent delivery catheter system 10 is sized to fit within an introducer sheath (not shown) and/or a guide catheter (not shown) to navigate to the desired vascular site. In enteral applications, the rapid exchange stent delivery catheter system is sized to fit within an endoscope (not shown), to navigate to the desired enteral site, and to enable expansion of a self-expanding stent (such as a Wallstent® produced by Boston Scientific Corporation) sufficiently large to palliate an enteral stricture and allow digestive processes to occur.

The rapid exchange stent delivery catheter 100 includes an inner tubular member 120 slidably disposed in an outer tubular member 140. The outer tubular member 140 includes a lumen (not visible) extending therethrough to slidably accommodate the inner tubular member 120. The inner tubular member 120 includes a guidewire lumen 130 (shown in FIG. 5A) extending through a distal portion thereof to accommodate the guidewire 30.

To provide rapid exchange capability for the rapid exchange stent delivery catheter 100, the guidewire 30 exits through a guidewire opening 170 in the outer tubular member 140 as will be discussed in greater detail with reference to FIGS. 3, 7A and 7B. The guidewire 30 extends through a relatively short guidewire lumen and enters through a distal guidewire opening in the inner tubular member 120, as will be discussed in greater detail with reference to FIGS. 4, 5A and 5B. In practice, the device 100 may be inserted over the guidewire 30 from the tip end first.

A proximal handle 122 is connected to a proximal portion 124 of the inner tubular member 120. Similarly, a distal handle 142 is connected to a proximal portion 144 of the outer tubular member 140. The distal handle 142 may be longitudinally displaced relative to the proximal handle 122 to selectively expose or cover the self-expanding stent 20, which is disposed about a distal portion of the inner tubular member 120. In FIG. 1, the distal handle 142 has been longitudinally displaced in the distal direction relative to proximal handle 122 such that the outer tubular member 140 covers the self-expanding stent 20. In FIG. 2, the distal handle 142 has been longitudinally displaced in the proximal direction relative to proximal handle 122 to retract the outer tubular member 140 relative to the inner tubular member 120 to expose and deploy the self-expanding stent 20.

Figures 3, 4, 5A, 5B, 6:
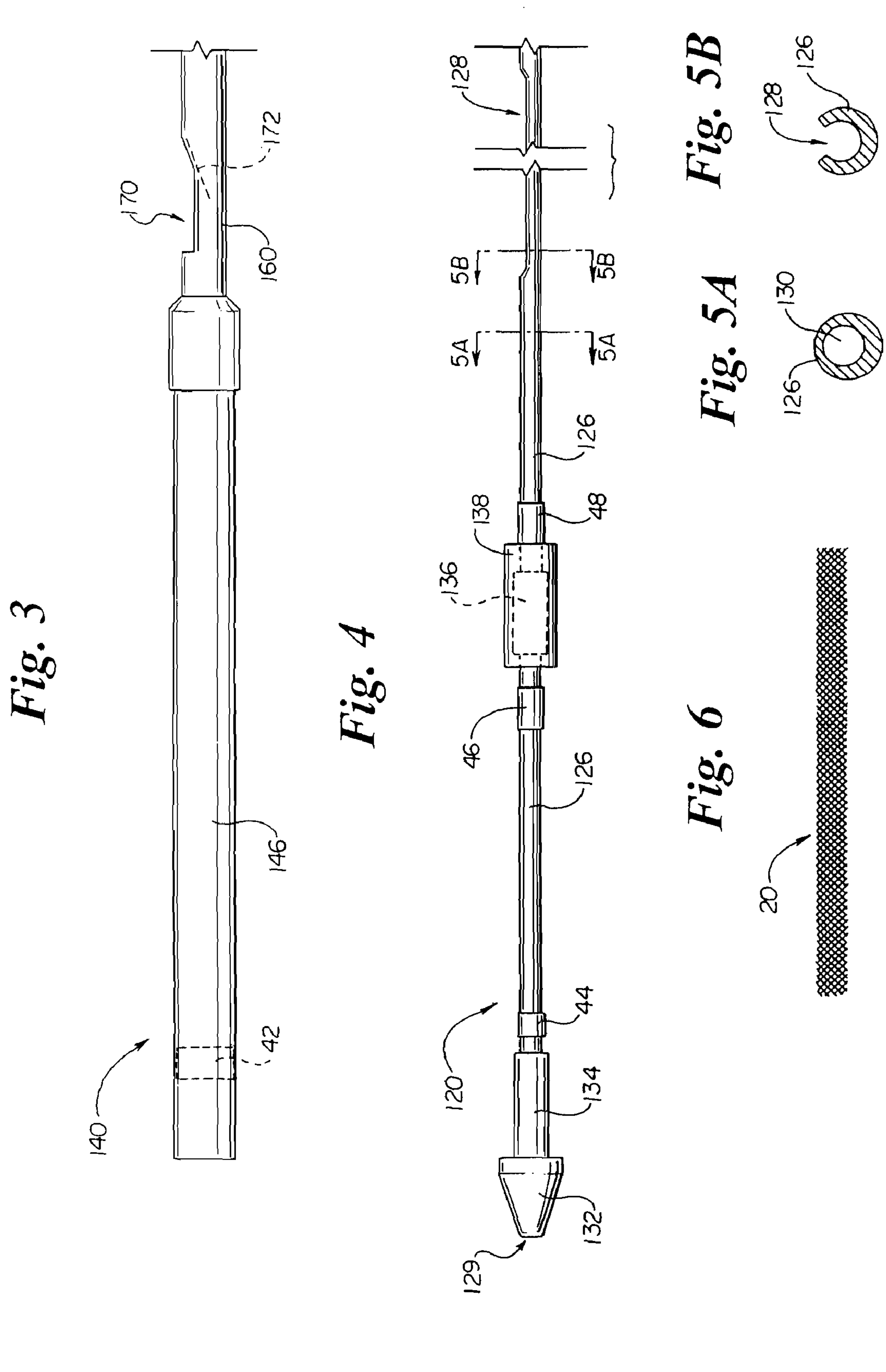
FIG. 3 is a plan view of a distal portion of the outer tubular member of the rapid exchange catheter illustrated in FIG. 1.
FIG. 4 is a plan view of an inner tubular member of the rapid exchange catheter illustrated in FIG. 1.
FIGS. 5A and 5B are cross-sectional views taken along lines 5A-5A and 5B-5B, respectively, in FIG. 4.
FIG. 6 is a plan view of a self-expanding metallic stent suitable for delivery by the rapid exchange catheter illustrated in FIG. 1.

With additional reference to FIG. 3, the outer tubular member 140 includes, from the proximal end to the distal end, a proximal portion 144, a main outer portion (not visible) a guidewire sleeve 160 and a distal outer portion 146. The proximal end of the proximal outer portion 144 is connected to the distal handle 142. The distal handle 142 may be injection molded over the proximal outer portion 144. The distal end of the proximal outer portion 144 is connected to the proximal end of the main outer portion (not visible). The distal end of the main outer portion (not visible) is connected to the proximal end of the guidewire sleeve 160, and the distal end of the guidewire sleeve 160 is connected to the proximal end of the distal outer portion 146. The various portions of the outer tubular member 140 may be connected by adhesive, by thermal means or by any other suitable means known to those skilled in the art.

For biliary applications, the proximal outer portion 144 may be formed of PEBAX®, having a length of approximately 8.0 inches (20.3 cm), an outside profile of approximately 0.120 inches (9 F) (0.30 cm), and an inside diameter of approximately 0.083 inches (0.21 cm). The guidewire sleeve 160 is discussed in greater detail with reference to FIGS. 7A and 7B. The main outer portion (not visible) may be formed of PEBAX®/wire braid/PTFE composite, having a length of approximately 55.0 inches (140 cm), an outside profile of approximately 6 F (0.079 inches), and an inside diameter of approximately 0.057 inches (0.145 cm). The distal outer portion 146 may be formed of PEBAX®/wire braid/PTFE composite, having a length of approximately 10.6 inches (27 cm), an outside profile of approximately 8 F (0.105 inches), and an inside diameter of approximately 0.090 inches (0.229 cm).

For an enteral application, the proximal outer portion 144 may be formed of PEBAX®, having a length of approximately 8.0 inches (20.3 cm), an outside profile of approximately 0.120 inches (9 F) (0.30 cm), and an inside diameter of approximately 0.083 inches (0.21 cm). The main outer portion (not visible) may be formed of PEBAX®/wire braid/PTFE composite, having a length of approximately 55.0 inches (140 cm), an outside profile range of approximately 6 F-8 F (0.079-0.105 inches), and an inside diameter of approximately 0.057 inches (0.145 cm). The distal outer portion 146 may be formed of PEBAX®/wire braid/PTFE composite, having a length of approximately 10.6 inches (27 cm), an outside profile of approximately 10 F (0.131 inches), and an inside diameter of approximately 0.113 inches (0.286 cm). Depending upon the size of the stricture to be palliated, longer or larger distal outer portions may be used as well.

A radiopaque marker band 42 may be disposed adjacent the distal end of the distal outer portion 146 to facilitate radiographic placement of the catheter 100 and to radiographically indicate the position of the outer tubular member 140 relative to the inner tubular member 120 to aid in deploying the self-expanding stent 20.

With additional reference to FIGS. 4, 5A and 5B, the inner tubular member 120 includes a distal inner portion 126 connected to the distal end of the proximal inner portion 124. The proximal inner portion 124 and the distal inner portion 126 are essentially the same, except the proximal inner portion 124 is reinforced with a stainless steel hypotube. The inner portions 124/126 may be formed of PEEK, having a length of approximately 88.6 inches (225 cm), an outside profile of approximately 0.052 inches (0.13 cm), and an inside diameter of approximately 0.037 inches (0.094 cm). A jacket formed of LDPE, having a length of approximately 5.9 inches (15 cm), an outside profile of approximately 0.080 inches (0.20 cm), and an inside diameter of approximately 0.055 inches (0.14 cm) may be disposed about the inner member 120 to consume the clearance between the inner member 120 and the outer member 140 proximal of the stent 20 to prevent kinking. The various portions of the inner tubular member 120 may be connected by adhesive, by thermal means or by any other suitable means known to those skilled in the art.

A distal head 132 is connected to the distal end of the distal inner portion 126 to limit distal displacement of the outer tubular member 140. A distal bond region 134 is disposed immediately proximal of the distal head 132. A holding sleeve 136 and a stent cup 138 prevent slippage of the stent 20. Radiopaque marker bands 44/48 are disposed on the distal inner portion 126 and are separated by a distance approximately equal to the length of the stent 20. The distal outer portion 146 of the outer tubular member 140 contains the self-expanding stent 20 during delivery.

The distal inner portion 126 includes a proximal guidewire opening 128 and a distal guidewire opening 129. A guidewire lumen 130 extends between the proximal guidewire opening 128 and the distal guidewire opening 129 to accommodate the guidewire 30 therein. The proximal guidewire opening 128 has a length which is greater than the length of the guidewire opening 170 of the guidewire sleeve 160. The length of the proximal guidewire opening 128 is sufficient to allow longitudinal displacement of the outer tubular member 140 relative to the inner tubular member 120 to permit full exposure and deployment of the self-expanding stent 20. The length of the proximal guidewire opening 128 is preferably slightly longer than the length of the constrained portion of the stent 20 to avoid wedging the guidewire 30 between the inner tubular member 120 and the outer tubular member 140 prior to full deployment of the stent 20.

The guidewire lumen 130 may be eccentrically positioned in the distal inner portion 126 as seen in FIGS. 5A and 5B. For example, the upper wall may have a thickness of approximately 0.003 inches and the lower wall may have a thickness of approximately 0.011 inches. The upper thinner wall portion may be removed (skived) to define the proximal guidewire opening 128. By removing only the thin-walled portion of the distal inner portion 126, the column strength of the inner tubular member 120 is not significantly compromised.

A solid mandrel (not shown) may be inserted into the proximal lumen (not visible) of the inner tubular member 120 proximal of the guidewire opening 128 for improved column strength. The solid mandrel may be formed of stainless steel having an outside diameter of approximately 0.030 inches with a tapered end. A stainless steel hypotube (not shown) having an outside diameter of approximately 0.079 inches may be disposed about the proximal inner portion 124 for added column strength and durability. The proximal handle 122 may be injection molded over the proximal end of the hypotube and the proximal end of the proximal inner portion 124.

A distal radiopaque marker 44 is disposed on the distal inner portion 126 to radiographically mark the distal end of the stent 20. A proximal radiopaque marker 48 is disposed on the distal inner portion 126 to radiographically mark the proximal end of the stent 20. A mid radiopaque marker 46 is disposed on the distal inner portion 126 distal of the holding sleeve 136 to radiographically facilitate deployment of the stent 20.

With reference to FIG. 6, the stent 20 may comprise any self-expanding stent suitable for enteral, biliary or intravascular applications. For example, the self-expanding stent 20 may comprise a metallic stent commercially available from Boston Scientific Corporation under the trade name Wallstent®.

Figure 7A:
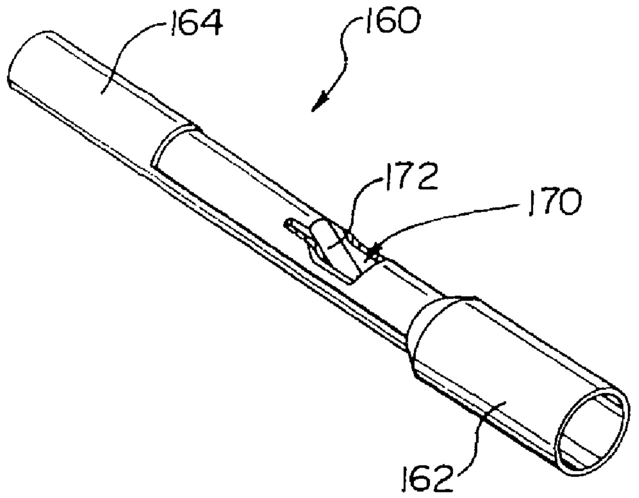
FIG. 7A is an isometric view of a guidewire sleeve of the outer tubular member illustrated in FIG. 3.
Figure 7B:
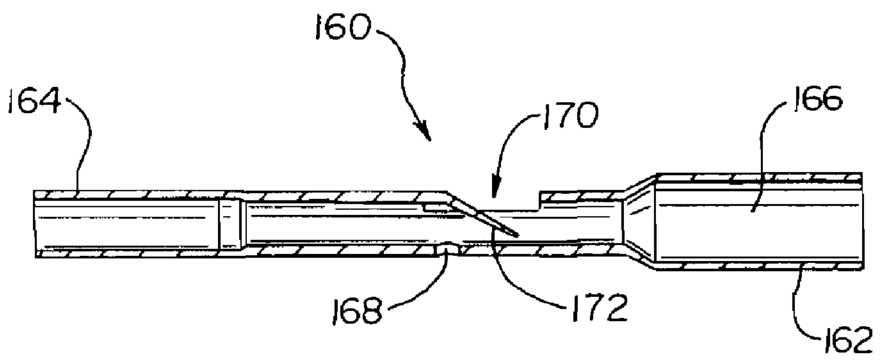
FIG. 7B is a longitudinal section view of a guidewire sleeve illustrated in FIG. 7A.

With reference to FIGS. 7A and 7B, the guidewire sleeve 160 includes a proximal portion 164, a distal portion 162 and a lumen 166 extending therethrough. The distal portion 162 is flared to fit over and be connected to the distal outer portion 146. The proximal portion 164 is sized to fit within and be connected to the main outer portion.

A guidewire opening 170 extends through the exterior wall of the guidewire sleeve 160. A ramp 172 extends from the exterior wall into the lumen 166. When assembled, the ramp 172 extends through the proximal guidewire opening 128 of the inner tubular member 120 and into the guidewire lumen 130. The ramp 172 is moveable within the proximal guidewire opening 128 to facilitate a smooth transition of the guidewire 30 from the guidewire lumen 130 to exterior of the catheter 100, regardless of the position of the outer tubular member 140 relative to the inner tubular member 120.

The guidewire sleeve 160 may have a length of approximately 1.0 inch, a distal outside diameter of approximately 0.122 inches, a proximal outside diameter of approximately 0.087 inches, a distal inside diameter of approximately 0.107 inches, and a proximal inside diameter of approximately 0.070 inches. The ramp 172 may be an integral extension of the exterior wall of the guidewire sleeve 160 and may have a length of approximately 0.090 inches and a width of approximately 0.50 inches. The ramp 172 may extend into the lumen 166 at an angle of approximately 30 degrees.

The guidewire sleeve 160 may be an integral part of the outer tubular member 140 but is preferably a separately manufactured component. For example, the guidewire sleeve 160 may be formed of injection molded nylon or polypropylene. If the guidewire sleeve 160 is injection molded, manufacturing artifacts such as hole 168 may be filled or removed depending on the particular application. By manufacturing the guidewire sleeve 160 separately, more manufacturing flexibility and efficiency are achieved. For example, the guidewire sleeve 160 may be made of a material that is not melt sensitive or that is readily bonded to facilitate connection to other catheter components using adhesive or thermal means. In addition, the guidewire sleeve 160 may be inspected prior entering the production floor to eliminate non-conforming parts and increase efficiency. Further, the dimensions may be controlled better to provide greater consistency at bond sites. These and other advantages not specifically mentioned herein may be obtained by manufacturing the guidewire sleeve 160 as a separate component, but such is not essential to the present invention.

Figure 8A:
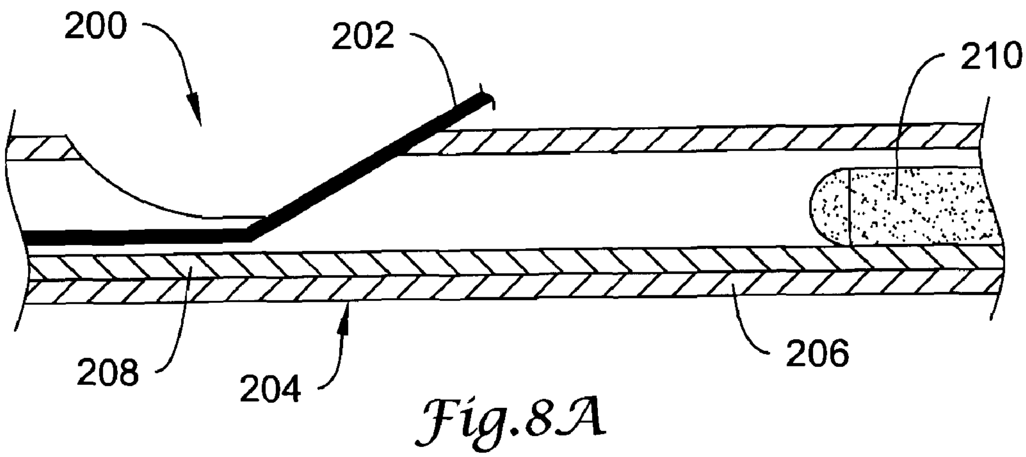
FIGS. 8A-8C are longitudinal sectional views of a guidewire entry port as a self-expanding stent is released for an embodiment corresponding to FIG. 1.
Figure 8B:
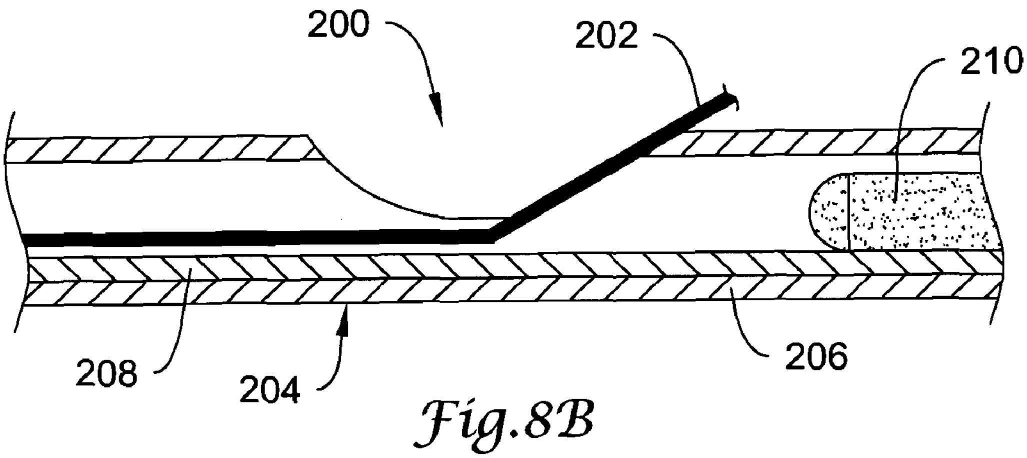
Figure 8C:
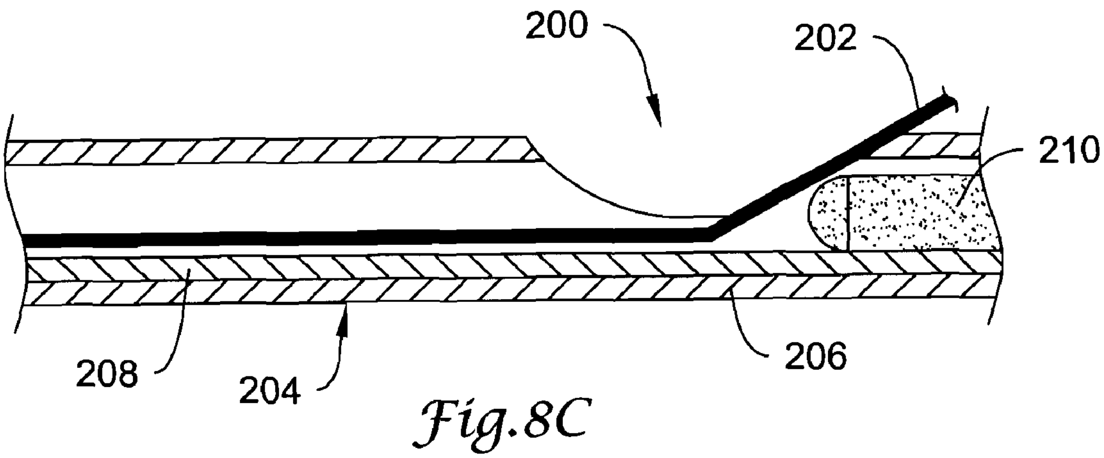

FIGS. 8A-8C are longitudinal sectional views of a guidewire entry port as a self-expanding stent is released for an embodiment corresponding to FIG. 1. The illustrative guidewire entry port 200 is shown having a guidewire 202 exiting the catheter 204. The catheter has an outer member 206, an inner member 208, and a mandrel 210. The mandrel 210 may be disposed, as noted above, within the inner member 206 to provide improved column strength over a proximal portion of the catheter.

FIG. 8A corresponds to a configuration wherein a stent is constrained by the outer member 206. As the inner member is slide distally with respect to the outer member 206, the mandrel 210, which is within the inner member 206, slides distally as well, as shown in FIG. 8B. FIG. 8C illustrates the configuration at the guidewire entry port 200 when the stent is fully deployed. As shown, the mandrel 210 must be sized to stop short of the entry port 200 to avoid interfering with the guidewire 202.

A potential problem for the configuration of FIGS. 8A-8C is the distance between the distal end of the mandrel 210 and the guidewire entry port 200. The mandrel 210 is included to provide added column strength, but does not span the guidewire entry port 200. The outer member 206 is cut at the guidewire entry port 200, weakening the outer member 206. The inner member 208 is skived across the guidewire entry port 200, and is, therefore, also weakened. These three conditions make the region of the guidewire entry port 200 subject to crimping due to relative weakness as compared to adjacent locations. It should also be noted that as the catheter is advanced, the stent is constrained as shown in FIG. 8A. This is the period in which the pushability of the catheter is most important, since once the stent is deployed, the catheter need not be advanced further. Yet the configuration for advancement is the time in which the catheter is weakest in the region of the guidewire entry port 200 because the mandrel 210 stops proximally thereof.

A further problem may occur when the stent is to be deployed. In particular, when relative pushing and pulling occurs between the inner member 208 and outer member 206, there is a potential for the catheter to deflect, causing inaccurate stent placement. For example, as the outer member 206 is withdrawn to deploy the stent (not shown), the skived inner member 208 can deflect at a location in the skived region (particularly to the side that is skived), causing the distal end of the catheter to deflect. Likewise, if, at a stage of partial deployment, it is determined that stent placement is incorrect, a decision may be made to seek to push the outer member distally to pull the stent back into a restrained position. Again, such a step can create lateral deflection. At locations where the guidewire is disposed within the catheter, it is easier to retain a straight configuration, because the guidewire provides at least some support to the catheter. However, this support is not as easily provided proximate to and proximal of the guidewire port.

Figure 9:
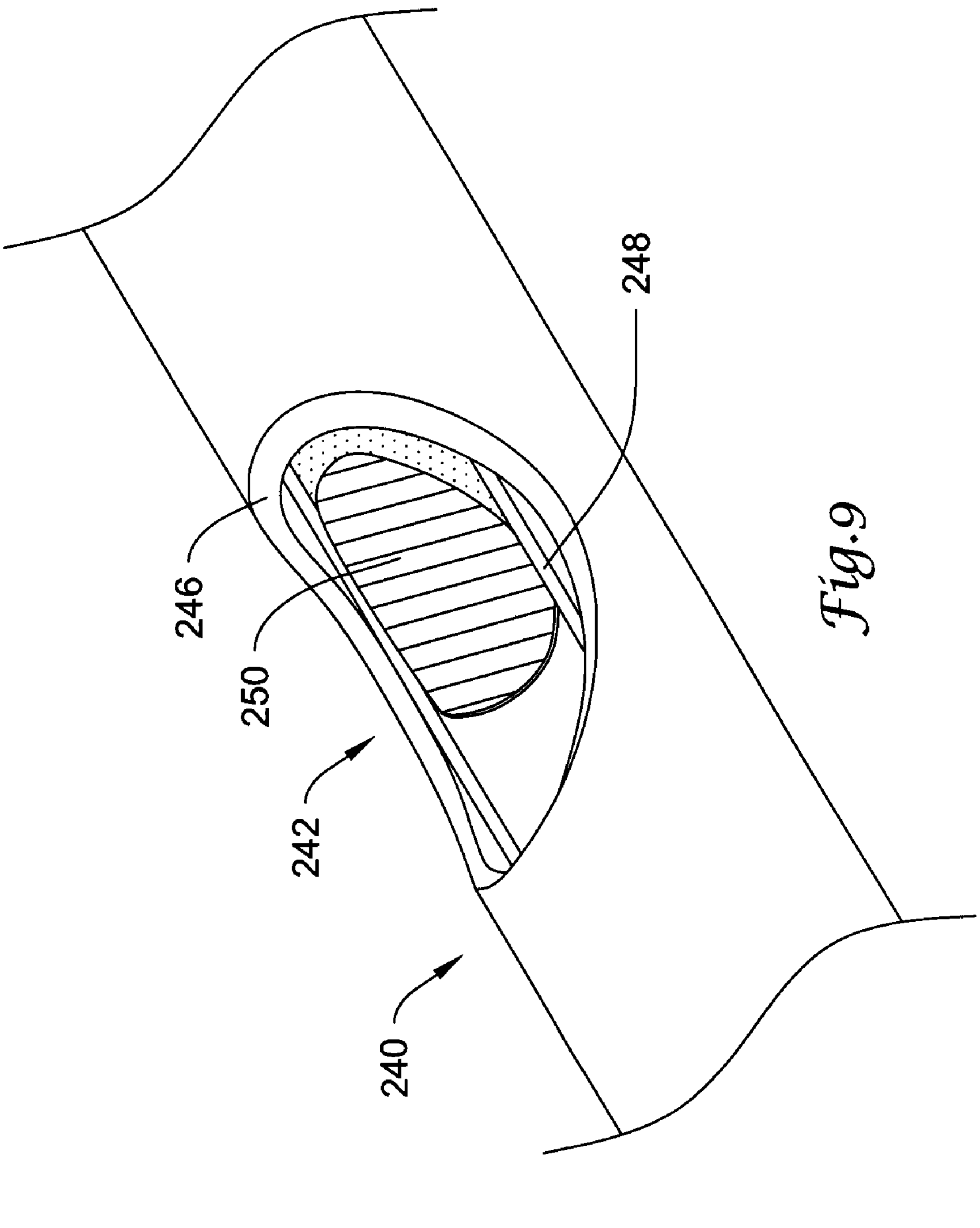
FIG. 9 is an isometric view of a guidewire entry ramp for another embodiment having a ramp-ended mandrel.

FIG. 9 is an isometric view of a guidewire entry ramp for another embodiment having a ramp-ended mandrel. The catheter 240 includes a guidewire entry port 242, outer member 246, inner member 248, and a mandrel 250 having a slanted or ramp-shaped distal end. While the FIG. 7A illustrates forming a ramp using the outer member, FIG. 9 instead uses a specially shaped mandrel 250. This modification allows for a simpler treatment of the outer member 246. By having the mandrel 250 form the ramp for causing a guidewire to exit the catheter, pushability may be improved in the region of the guidewire entry port 242, since the guidewire provides support in and distal of the guidewire entry port 242, and the mandrel extends to the guidewire entry port 242.

Figures 10, 12A, 12B, 12C, 12D, 12E, 12F:
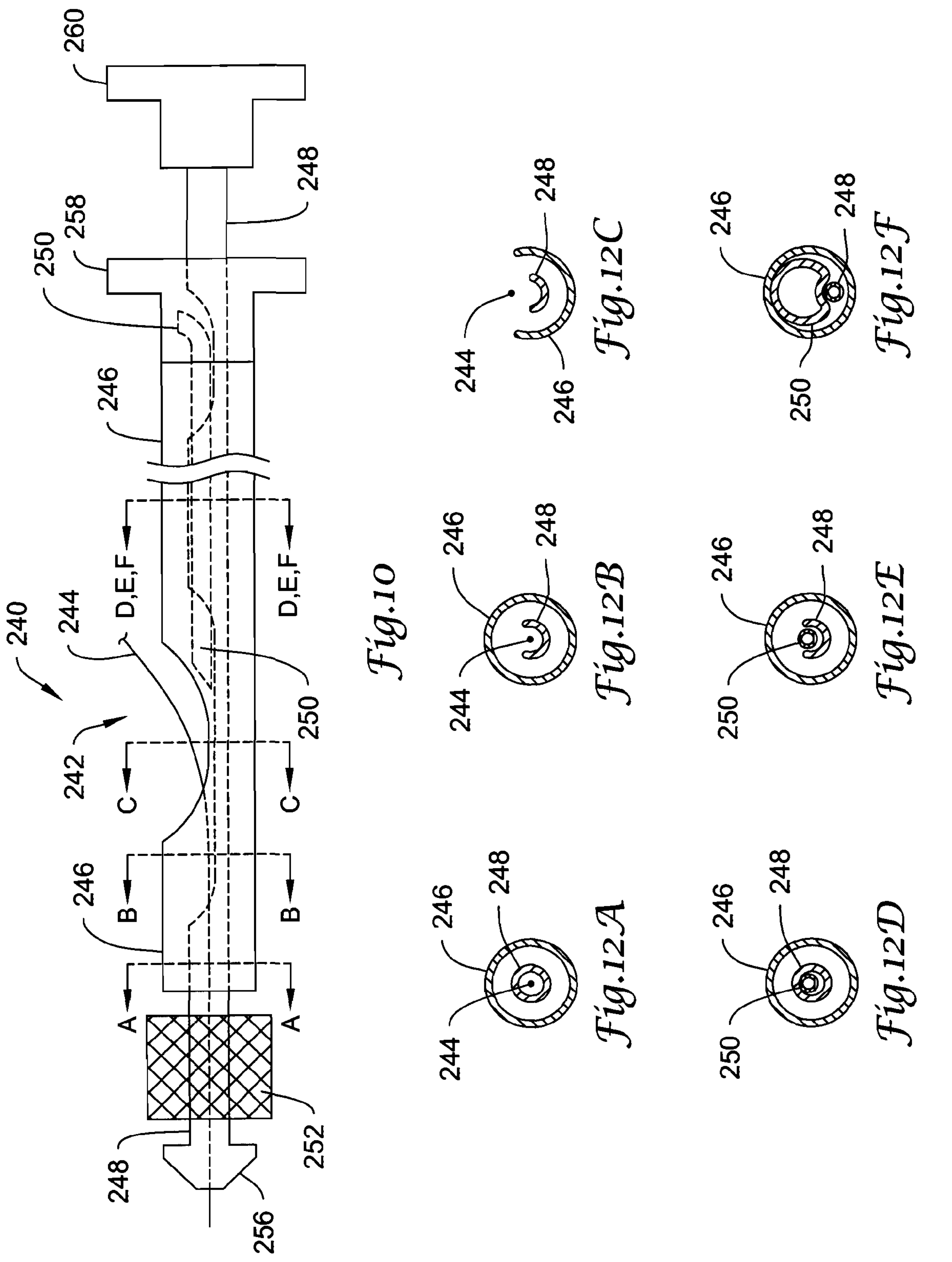
FIG. 10 is a plan view of a rapid exchange stent delivery catheter using a ramp-ended mandrel.
FIGS. 12A-12F are cross sectional views taken along lines A-A, B-B, C-C, and D,E,F-D,E,F, respectively, in FIG. 10.

FIG. 10 is a plan and partial cut-away view of a rapid exchange stent delivery catheter according to FIG. 9. The catheter 240 is shown having a guidewire port 242 which allows a guidewire 244 to exit the catheter 240. The inner member 248 is shown as carrying a stent 252 (shown by cutting away a portion of the outer member 246) and having a distal cap 256. The inner member 248 may be crimped or skived across the guidewire port 242. As illustrated by the placement of the guidewire 244, the inner member 248 does include an opening allowing entry of the guidewire 244 thereto and passage through a lumen in the inner member 248 to the distal end of the catheter 240.

The catheter 240 also includes two proximal end handles, a first handle 258 coupled to the outer member 246 and a second handle 260 coupled to the inner member 248. The handles 258, 260 allow a physician to easily slide the inner member 248 with respect to the outer member 246. As shown and in contrast to several of the above-noted designs, the mandrel 250 is attached to the first handle 258, such that it is coupled to the outer member 246 rather than the inner member 248.

Figure 11A:
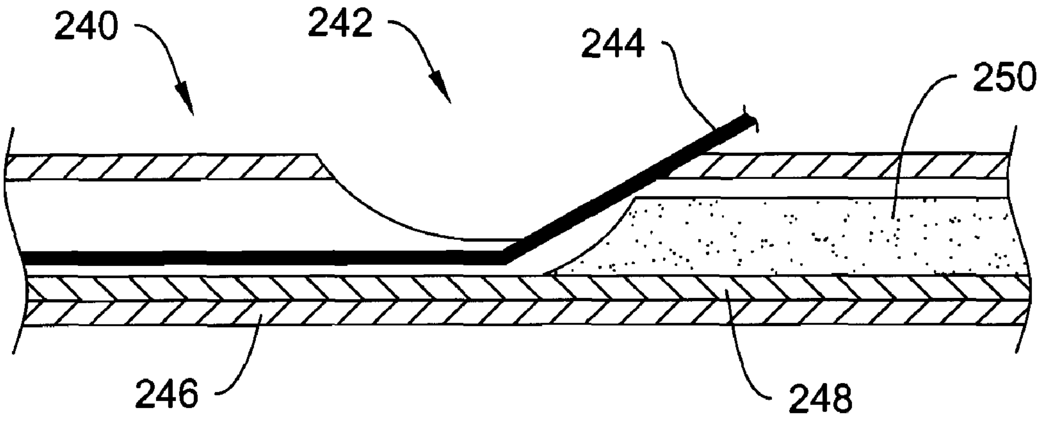
FIGS. 11A-11C are longitudinal sectional views of a guidewire entry port as a self-expanding stent is released for an embodiment corresponding to FIG. 10.
Figure 11B:
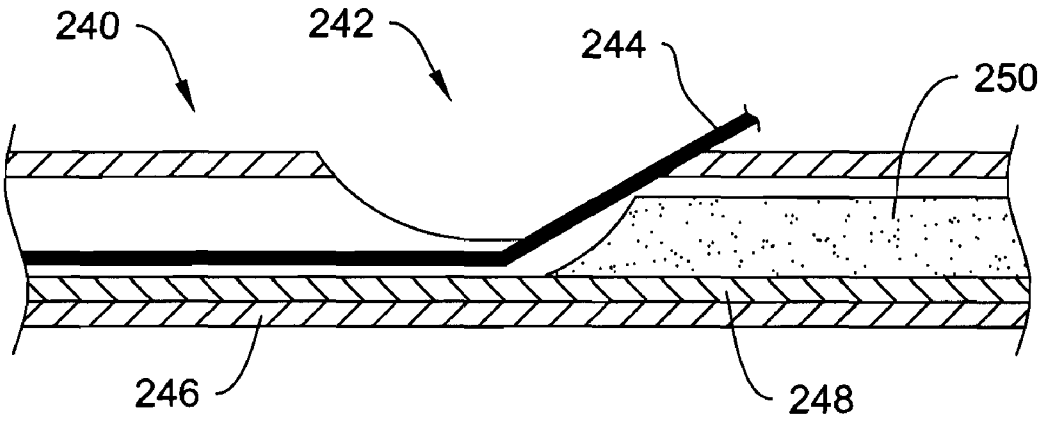
Figure 11C:
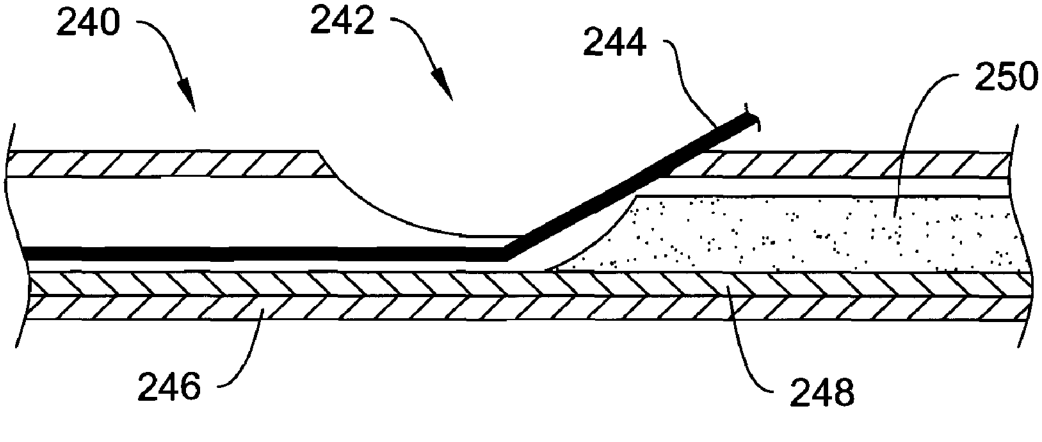

FIGS. 11A-11C are longitudinal sectional views of a guidewire entry port as a self-expanding stent is released for an embodiment corresponding to FIG. 10. FIG. 11A shows the guidewire 244 exiting the guidewire port 242 with the mandrel 250 in providing an exit ramp. As the stent is partially deployed in FIG. 11B, and fully deployed in FIG. 11C, the mandrel 250 does not move with respect to the guidewire port 242, since the port 242 and the mandrel 250 are coupled directly to the outer member 246. This means that, as illustrated in FIGS. 11A-11C, the mandrel 250 does not move with respect to the outer member 246 and the guidewire port 242. Thus, the added pushability provided by the mandrel 250 is made usable during insertion and advancement of the catheter 240, before deployment of the stent 252.

FIGS. 12A-12F are cross sectional views taken along lines A-A, B-B, C-C, and D,E,F-D,E,F, respectively, in FIG. 10. Note that FIGS. 12D-12F are alternatives to one another illustrating different proximal configurations for the mandrel 250 and the inner member 248. As shown in FIG. 12A, the outer member 246 and inner member 248 are generally coaxial. The guidewire 244 passes through a lumen defined by the inner member 248.

FIG. 12B is closer to the guidewire port 242 (FIG. 10), and shows that a portion of the inner member 248 has been skived off or otherwise removed to allow the guidewire 244 to enter the lumen of the inner member 248. At the guidewire port 242 (FIG. 10), as shown in FIG. 12C, both the inner member 248 and the outer member 246 have a generally crescent shape allowing the guidewire 244 to enter the catheter. Several alternative configurations proximal of the guidewire port 242 (FIG. 10) are shown in FIGS. 12D-12F.

FIG. 12D corresponds generally to that shown in FIG. 10, illustrating that the inner member 248 resumes a tubular shape proximal of the guidewire port 242 (FIG. 10) and the mandrel 250 passes therethrough. In order to have the mandrel 250 coupled to the first handle 258 (FIG. 10), the inner member 248 may be skived or otherwise have a portion removed near the proximal end of the inner member 248. This allows the mandrel 250 to pass outside the inner member 248 and couple to either the outer member 246 or the first handle 258 (FIG. 10). This coupling limits relative axial movement of the outer member 246 and the mandrel 250.

FIG. 12E corresponds to a first alternative configuration where the inner member 248 has a crescent shape (for example, by removing a portion of a hypotube) proximal of the guidewire port 242 (FIG. 10) to the proximal end, at least, of the mandrel 250. Another alternative is shown in FIG. 12F, where the inner member 248 is shown as a push or core wire. The mandrel 250 may be shaped to secure the inner member 248 wire in an un-kinked or bent configuration, as shown. For the embodiment of FIG. 12F, the wire portion of the inner member 248 may be attached by any of a number of methods (i.e., welding, brazing, or adhesive, for example) to the more distal crescent-shaped and/or tubular portions of the inner member 248. Although the mandrel 250 is shown as being significantly larger than the inner member 248 for purposes of illustration, this need not be the case.

Figure 13:
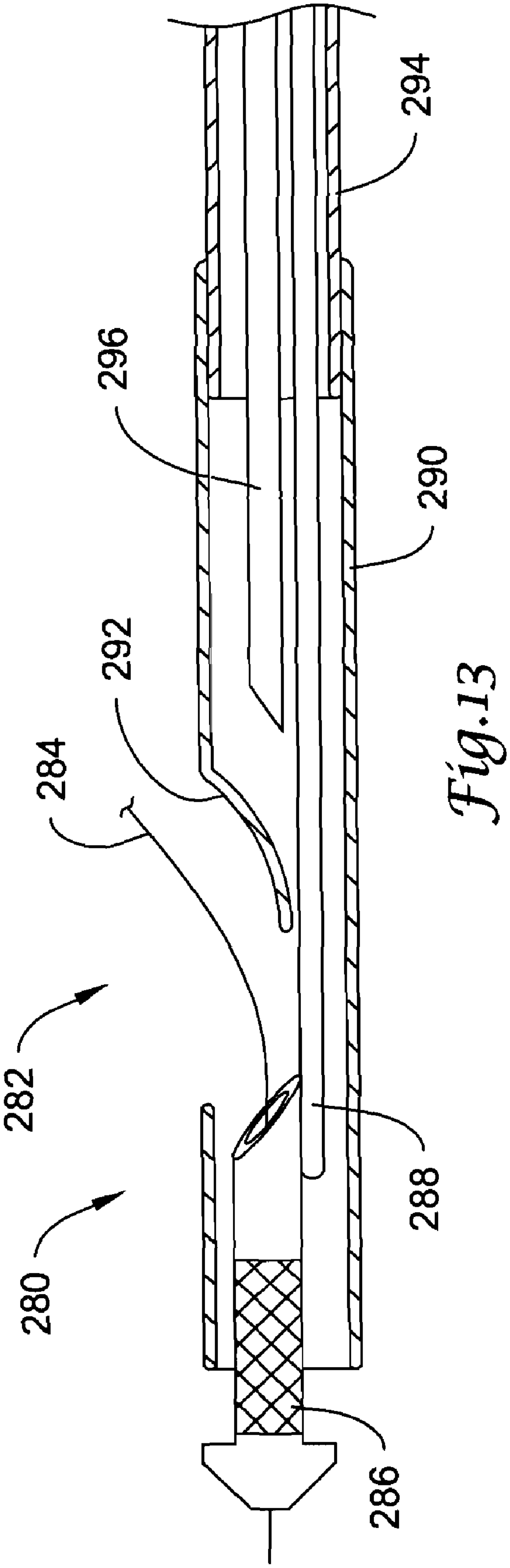
FIG. 13 is a longitudinal sectional view of a guidewire entry port and distal end of a rapid exchange stent delivery catheter having a proximal push wire.

FIG. 13 is a longitudinal sectional view of a guidewire entry port and distal end of a rapid exchange stent delivery catheter 280 having a proximal push wire. The guidewire entry port 282 allows a guidewire 284 to exit the catheter. An inner member includes a distal tubular section 286 and a proximal push member 288 which is illustrated in the form of a wire. The outer member includes an outer distal member 290, from which a flap has been used to make a ramp 292. The outer distal member 290 is secured to an outer proximal member 294.

In one embodiment, the outer proximal member 294 is a smaller bore hypotube, and the outer distal member 290 is a larger bore polymeric member. In another embodiment, the outer proximal member 294 takes the form of a dual lumen side-by-side elongate member. A mandrel 296 may optionally be included. The several integral parts of the catheter 280 may be secured together by any of a number of methods, including thermal and adhesive processes.

Figure 14A:
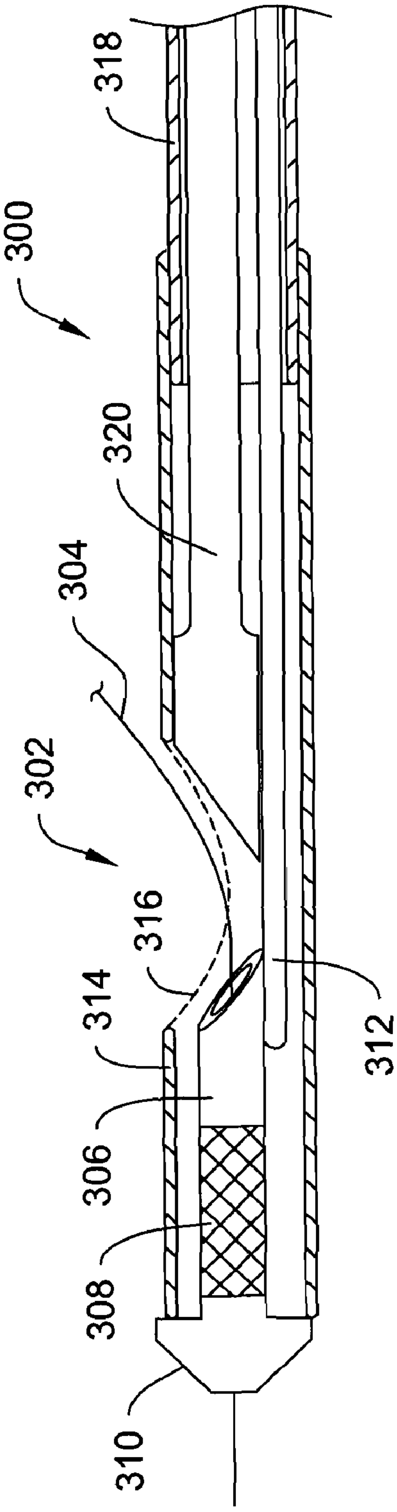
FIGS. 14A-14B are longitudinal sectional views of another guidewire entry port and distal end of a catheter having a ramp-shaped mandrel and a proximal push wire.
Figure 14B:
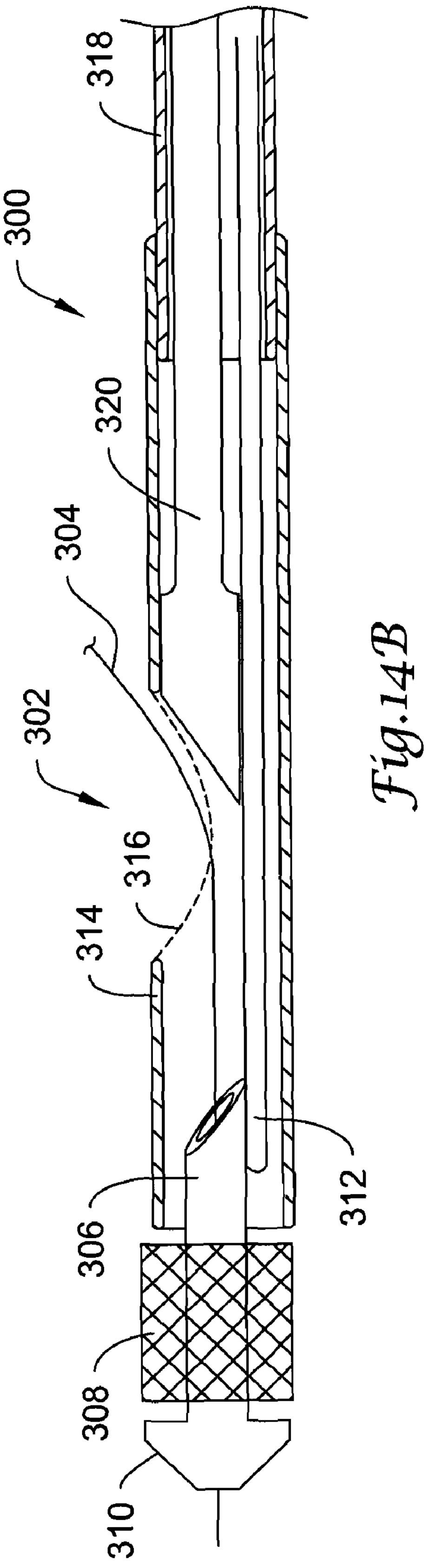

FIGS. 14A-14B are longitudinal sectional views of another guidewire entry port and distal end of a catheter having a ramp-shaped mandrel and a proximal push wire. Referring to FIG. 14A, the catheter 300 includes a guidewire port 302 where a guidewire 304 exits the catheter 300. An inner member includes a distal tubular member 306 on which a stent 308 is disposed, and which ends in a distal head 310. The distal tubular member 306 is attached on its outside, near its proximal end, to a push wire 312 that extends toward the proximal end (not shown) of the catheter 300.

A distal outer member 314 is illustrated as well, with the outer member 314 having been skived or trimmed to remove a portion for creating the guidewire port 302, as shown at 316. The distal outer member 314 is attached to a proximal outer member 318. A mandrel 320 having a ramp-shaped distal end is included, and may be secured in a manner which causes it to move axially in a one-to-one ratio with the outer members 314, 318.

In one embodiment, a handle at the proximal end (not shown) of the catheter 300 is attached to both the mandrel 320 and the proximal outer member 318. In another embodiment, the mandrel 320 may be secured to the proximal outer member 318 at some location along the length thereof. For example, if the proximal outer member 318 is provided as a hypotube, a metal mandrel 320 may be brazed or welded to the hypotube.

One known problem for some rapid exchange catheters having inner and outer members that are slidable with respect to one another is alignment. If the inner member is a tubular member along the length that crosses the guidewire port, then the opening in the inner member for the guidewire exit must align with the opening of the outer member for the guidewire exit port. Otherwise, the guidewire is subject to added friction or pinching at the guidewire exit port, making relative movement between the guidewire and the catheter difficult. However, if the inner member is not a tubular member across the guidewire port, which is the case for several embodiments herein (including FIGS. 14A-14B), the alignment problem is alleviated.

FIG. 14A illustrates the catheter 300 in a non-deployed configuration. To deploy the stent 308, the inner tubular member 306 is advanced by the combination of a pushing force applied to the push wire 312 and a pulling force applied to the proximal outer member 318. As the stent 308 passes the distal end of the outer member 314, it self-expands to unblock or palliate a stricture in a body lumen, as shown in FIG. 14B.

Figure 15:
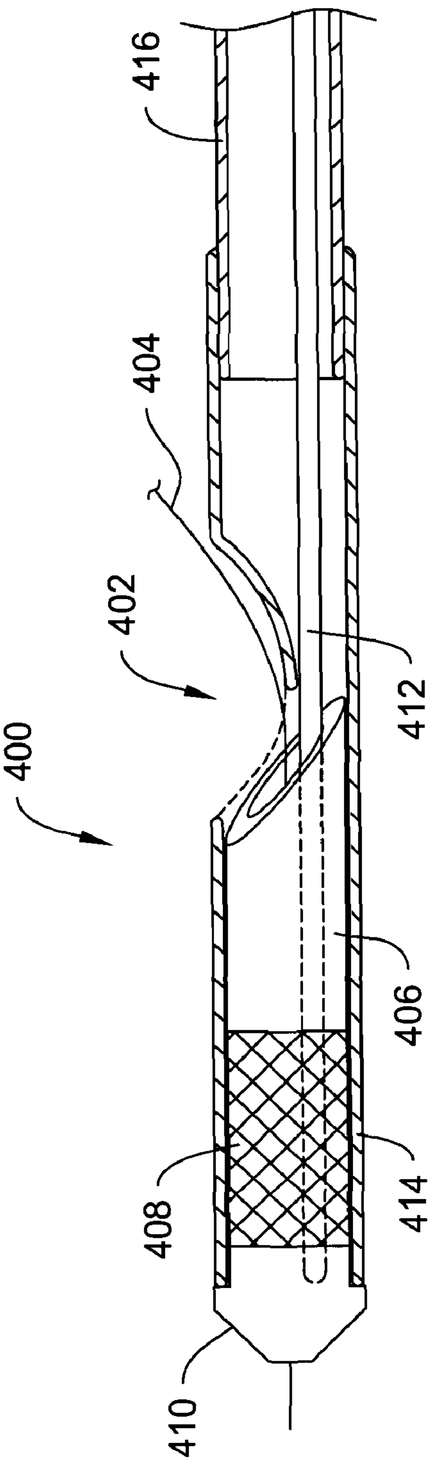
FIG. 15 is a longitudinal sectional view of yet another guidewire entry port and distal end of a rapid exchange stent delivery catheter.

FIG. 15 is a longitudinal sectional view of yet another guidewire entry port and distal end of a rapid exchange stent delivery catheter. The catheter 400 includes a guidewire port 402 allowing a guidewire 404 to pass from within the catheter 400 to the exterior. A distal tubular member 406 carries a stent 408 and is attached to a distal head 410. A push wire 412 is attached to the distal tubular member 406.

A distal outer member 414 has a ramp formed therein at the guidewire port 402. The ramp may be formed by any number of methods. For example, the ramp can be formed by making a partial circumferential cut in the distal outer member 414, making a longitudinal slit in the distal outer member extending proximally from the partial circumferential cut, using one or more mandrels to hold the cut portions in a desired ramp shape, and applying heat to cause melting or at least re-flow of the distal outer member 414 material. Instead of the longitudinal slit, the distal outer member 414 may be held in a crimped configuration and heated to form the ramp.

In FIGS. 13, 14A and 14B, the pushwires 288, 312 attach to the outside of the distal tubular members 286, 306. As shown in FIG. 15, the pushwire 412 attaches to the inside of the distal tubular member 406. As illustrated by FIG. 15, this inner attachment allows the distal tubular member 406 to be sized more closely to the size of the distal outer member 414. By extending the pushwire 412 well into the distal tubular member 406, indeed, to the distal head 410, the pushwire 412 is used to transmit the pushing force, allowing the distal tubular member itself to be a very thin-walled piece.

Figure 16:
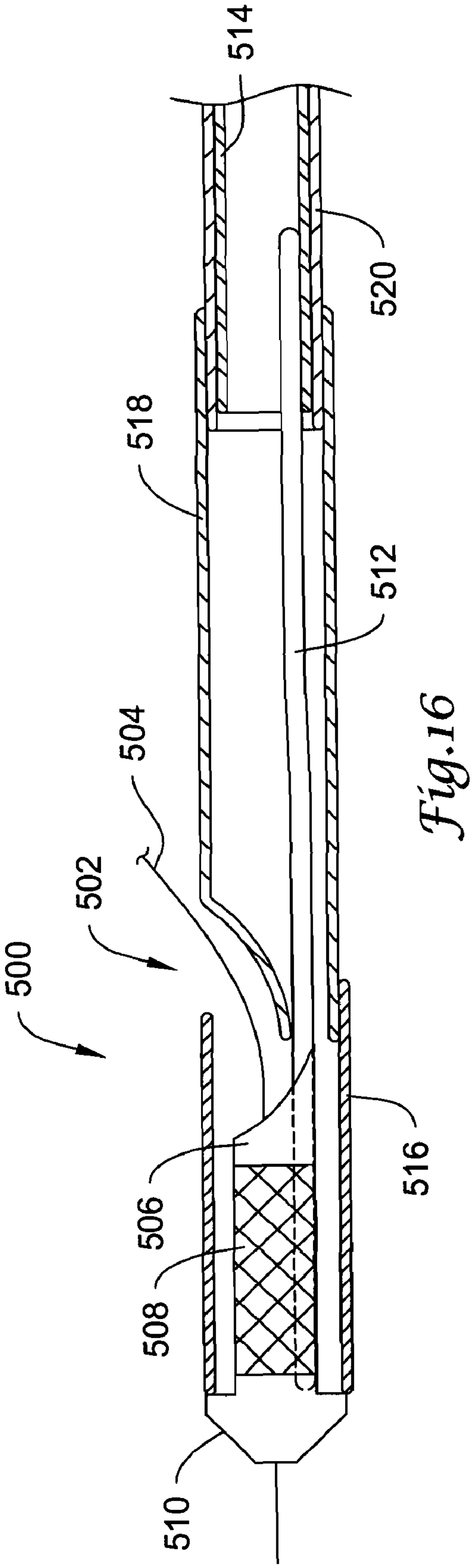
FIG. 16 is a longitudinal sectional view of still another guidewire entry port and distal end of a rapid exchange stent delivery catheter.

FIG. 16 is a longitudinal sectional view of still another guidewire entry port and distal end of a rapid exchange stent delivery catheter. The catheter 500 includes a guidewire port 502 allowing a guidewire 504 to exit the catheter 500. A distal inner member 506 carries a stent 508 and extends to a distal head 510. The distal inner member 506 is coupled to a pushwire 512, which spans the guidewire port 502 and couples to a proximal member 514 which is shown in the form of a round elongate member that may be hollow, filled, or solid.

The outside of the catheter 500 includes three main parts, a distal outer member 516, a midshaft 518, and a proximal member 520. The ramp for the guidewire port 502 is defined by the midshaft 518, which may be shaped by any number of methods such as the cut, slit and re-flow or crimp and melt methods discussed above with respect to FIG. 15. The distal outer member 516 may be attached during the steps of forming the ramp, or may be placed later. The midshaft 518 is also attached to the proximal member 520 which, in several embodiments, is a hypotube.

It should be noted that for several embodiments herein, the catheters may be considered “convertible”. For example, the catheter 500 can be initially placed over a first guidewire that exits the catheter at the guidewire port 502. If the first guidewire proves to be unsuitable for the particular lesion or stricture being treated (for example, it may be too flexible to pass a stricture, or may not be suitable for precise advancement), the guidewire may be withdrawn and a second guidewire advanced through the proximal inner member 514 to the ramp.

The inner members are movable with respect to the outer member; the ramp need not completely or tightly seal (indeed, too tight of a seal may impede relative movement needed to deploy the stent 508) thereabout. In vascular applications, blood is a relatively sticky fluid, so it is useful to provide tight seals to keep the blood from entering guidewire lumens and limiting guidewire movement. However, this problem is greatly reduced in biliary applications so that tighter seals are not always a necessity (though the fluids tend to be more corrosive and can create other problems). Because the second guidewire will advance to the back side of the ramp, it will be directed by the ramp to the location where the inner member (i.e., push wire 512) passes the ramp, and may pass by the ramp by passing adjacent the inner member (push wire 512). The second guidewire can then be advanced to the distal end of the catheter 500.

Figure 18:
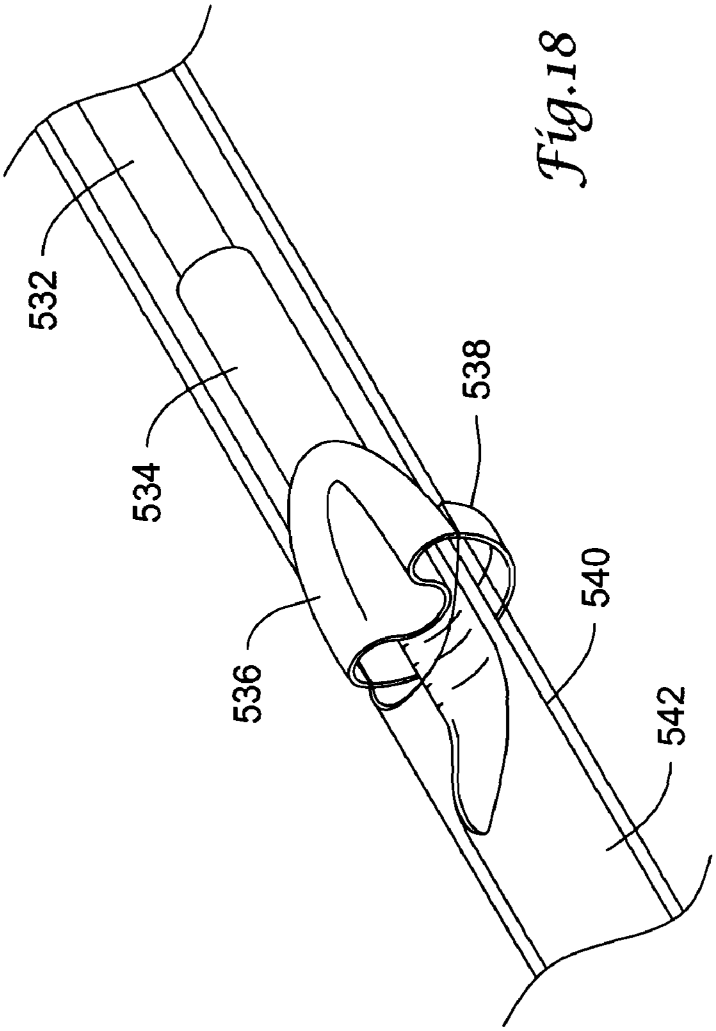
FIG. 18 is an isometric view of an assembled catheter incorporating the mandrel/ramp member and band of FIG. 17.
Figure 17:
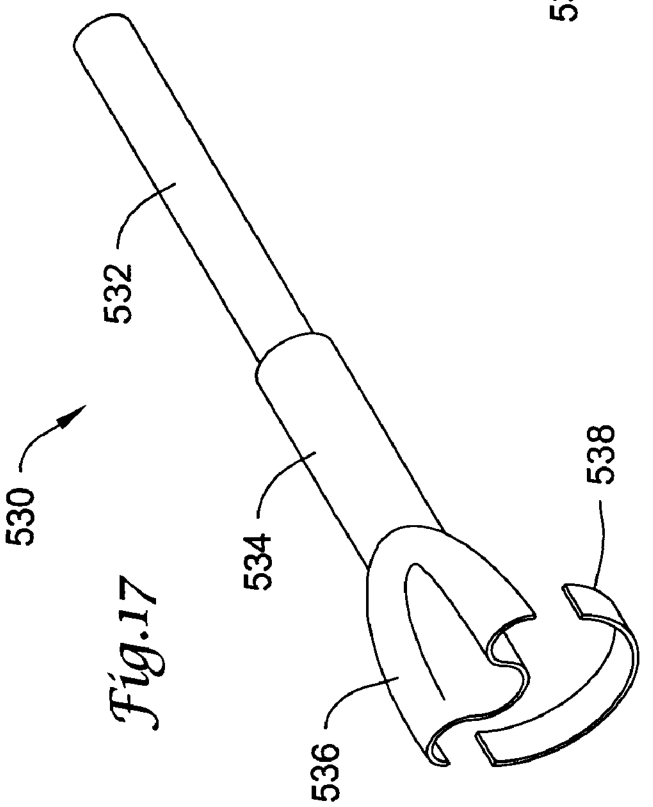
FIG. 17 is an exploded view of a mandrel/ramp member including a band to provide a guidewire entry port.

FIG. 17 is an exploded view of a ramp member including a band to provide a guidewire entry port. The mandrel/ramp member 530 is formed having a mandrel portion 532 coupled at its distal end of a ramp piece 534 having a ramp 536. To help secure the ramp piece 534 to the outer member (not shown), a band 538 is included. As shown in FIG. 18, the ramp 536 and band 538 are secured about the outer member 540, which at least partially encloses the inner member 542. The band 538 may be secured to the ramp 536 by any suitable manner, including the application of adhesives, welding, and/or snap fit.

Figure 19:
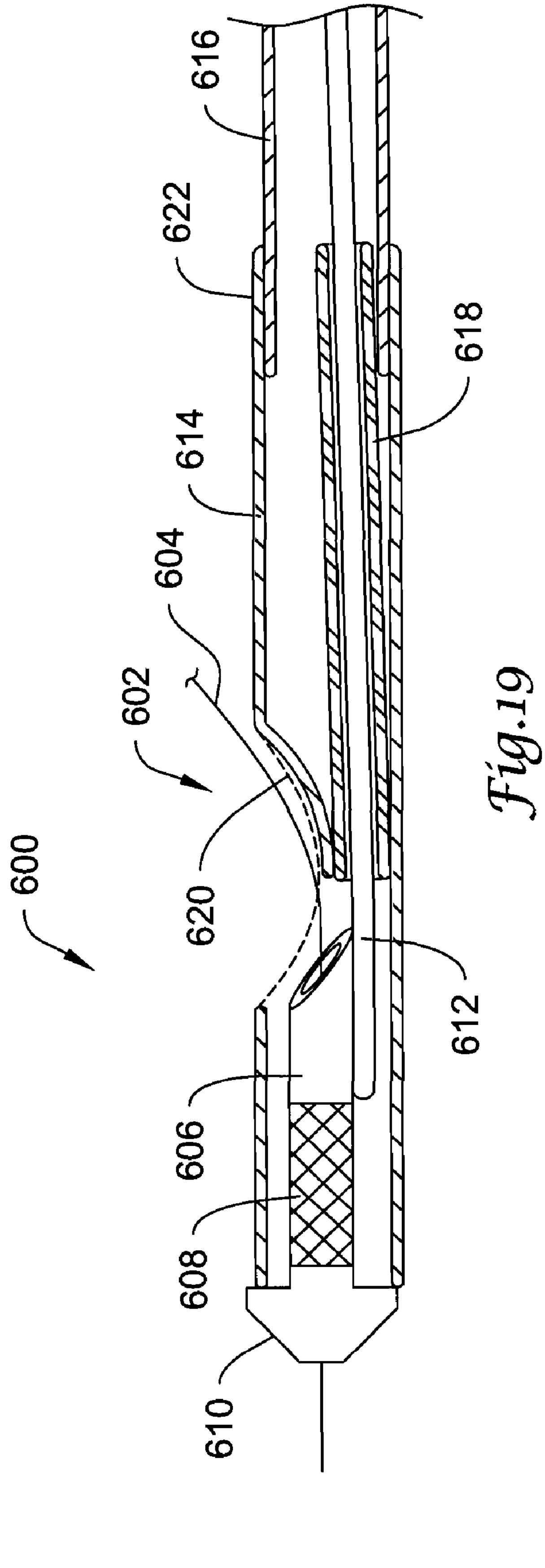
FIG. 19 is a longitudinal sectional view of a guidewire entry port and distal end of a rapid exchange stent delivery catheter including an intermediate tubular member across the guidewire entry port.

FIG. 19 is a longitudinal sectional view of a guidewire entry port and distal end of a rapid exchange stent delivery catheter including an intermediate tubular member across the guidewire entry port. The catheter 600 includes a guidewire port 602 allowing a guidewire 604 to exit the catheter 600. A distal tubular member 606 carries a stent 608 and ends in a distal head 610. The distal tubular member 606 is attached to a push wire 612 that passes to the proximal side of the guidewire port 602.

The distal outer member 614 is cut to remove a portion at the guidewire port 602. The proximal end of the distal outer member 614 is attached to a proximal outer member 616 that may be a polymeric or reinforced polymeric tube, but is preferably a hypotube. For the illustrative example of FIG. 19, the proximal end of the distal outer member 614 has been crimped or slit and compressed against the distal end of the proximal outer member 616 to achieve attachment thereto, as shown by the taper at 622. This enables use of a lower profile proximal outer member 616.

An intermediate tubular member 618 is also illustrated. The intermediate tubular member 618 is used to aid in making the ramp 620 that directs the guidewire 604 out of the catheter 600. To make the ramp, a first mandrel is passed through the intermediate tubular member 618, and the intermediate tubular member 618 is placed within the distal outer member 614. A partial circumferential cut is made in the distal outer member 614 to define the distal edge of the guidewire port 602.

Proximally of the cut, the distal outer member 614 is then crimped down to the intermediate tubular member 618. Additional mandrels may be placed to retain the patency of the distal outer member 614 during the next step, which includes heating the distal outer member 614 in the region of the ramp 620 to cause melting and/or reflow of the catheter 600 material. The intermediate tubular member 618 aids in providing pushability for the whole catheter 600, as well as providing directional control over the push wire 612 across the guidewire port 602.

Figure 20A:
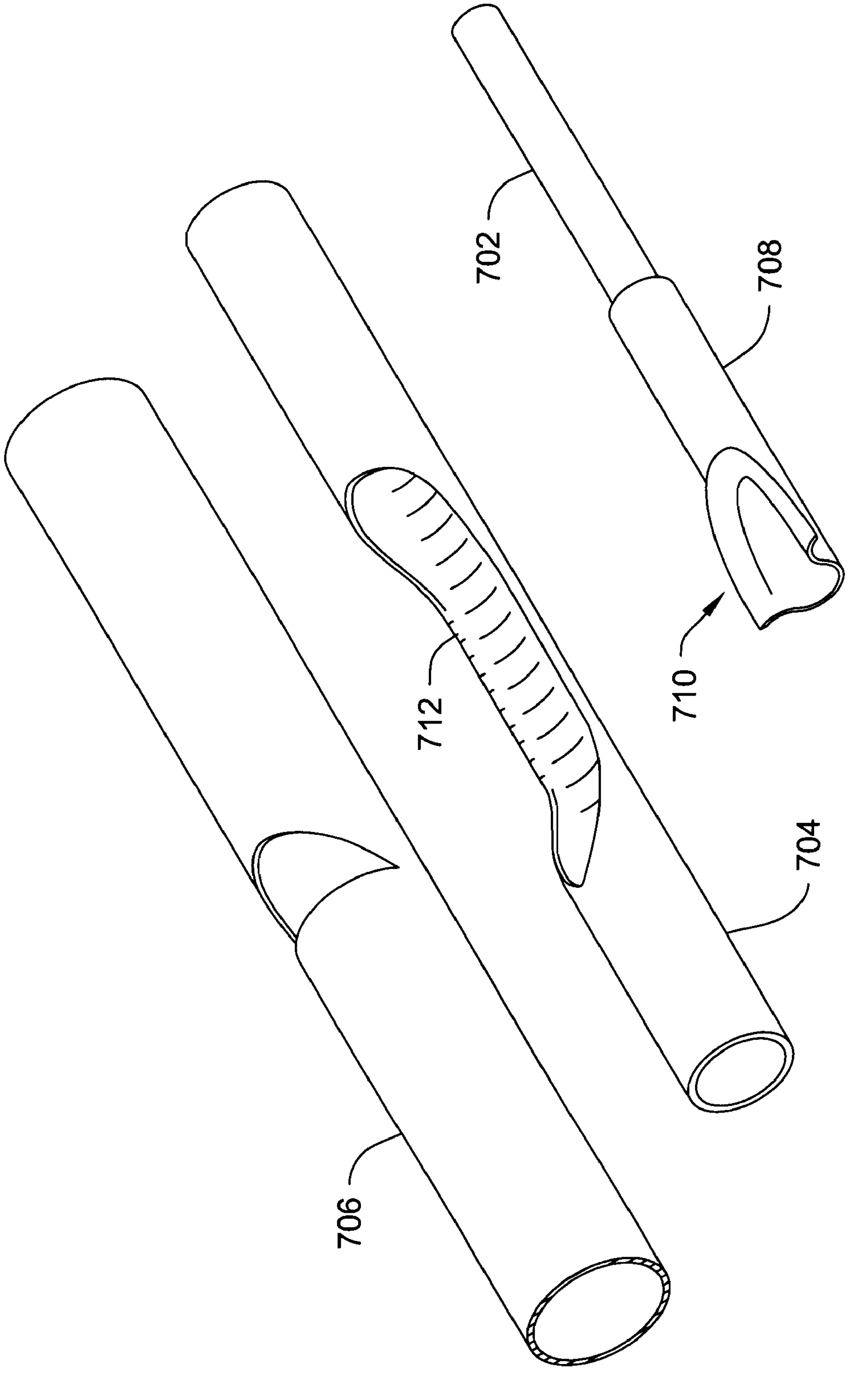
FIGS. 20A-20B are a partial side cross view and an exploded view of another illustrative embodiment wherein a ramp is coupled to an inner mandrel and extends out to the outer member.
Figure 20B:
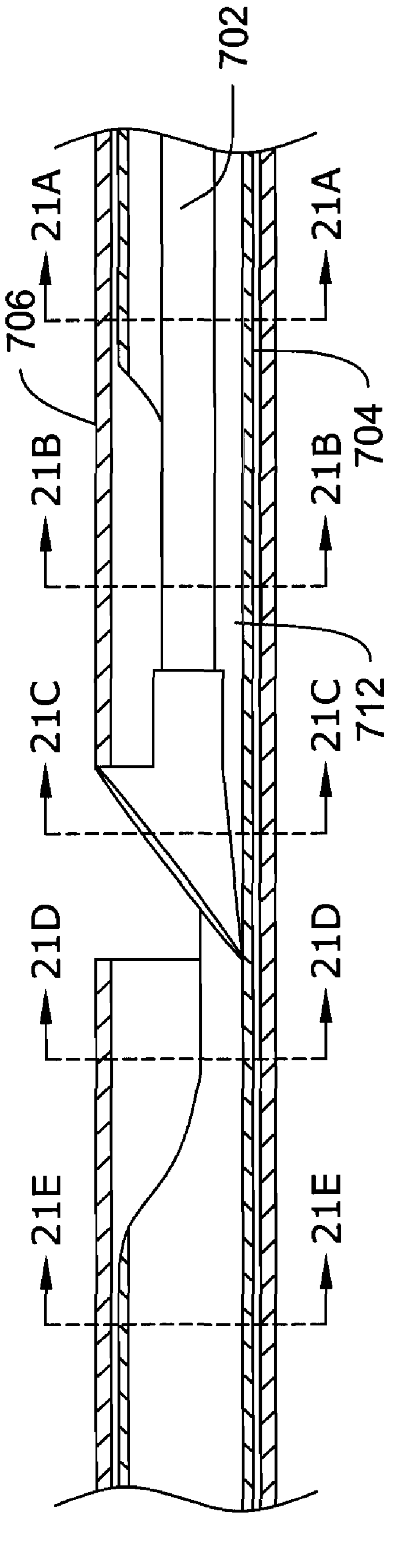

FIGS. 20A and 20B provide an exploded and side section view of another illustrative embodiment wherein a ramp is coupled to an inner mandrel and extends out to the outer member. The catheter 700 includes a mandrel 702, inner member 704 and outer member 706. The distal end of the mandrel 702 is connected to a ramp member 708 including guidewire ramp 710. The inner member 704 includes a skived portion 712. As shown, the ramp member 708 is secured to both the mandrel 702 and the outer member 706. In one such embodiment, the mandrel 702 may have an unsecured proximal end, and is provided for stiffness support. In another embodiment, the mandrel 702 may be secured near its proximal end to the outer member 706, or to an element secured to the outer member 706.

Figure 21A:
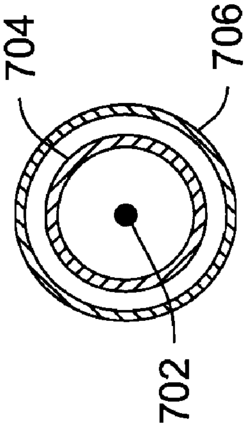
FIGS. 21A-21E are cross-sectional views taken along lines 21A-21A, 21B-21B, 21C-21C, 21D-21D, and 21E-21E, respectively of FIG. 20B.
Figure 21B:
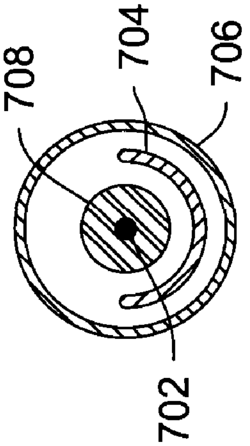

FIGS. 21A-21E are cross-sectional views taken along lines 21A-21A, 21B-21B, 21C-21C, 21D-21D, and 21E-21E, respectively, of FIG. 20B. As shown in FIG. 21A, the mandrel 702 is disposed within the inner member 704 and outer member 706. Moving distally to FIG. 21B, the mandrel 702 has been secured to the ramp member 708 near its distal end, at a location corresponding to the skived portion 712 of the inner member. The ramp member 708 may be secured to the mandrel 702 by any suitable method, for example, using heat, welding, adhesives, and/or insert molding, for example.

Figure 21C:
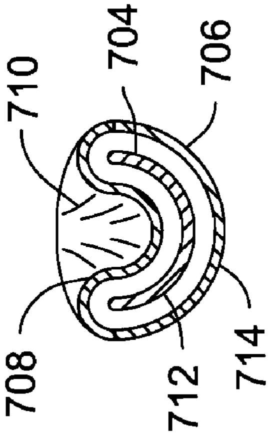

Going distally again to FIG. 21C, the ramp member 708 and the guidewire ramp 710 can be seen. The ramp member 708 is secured to the outer member 706 by any suitable method. The illustrative embodiment of FIG. 21C shows the ramp member 708 secured to the outer member 706 using a lap joint that is heat welded together, for example, with the use of a crescent shaped mandrel and a hot die, or by a laser method. Alternatively, an adhesive may also be used. Because the ramp member 708 is secured to both the mandrel 702 (FIG. 21B) and the outer member 706, there is no variable "gap" from the distal end of the mandrel 702 to the ramp 710 and/or the opening or skived portion 714 of the outer member 706.

Figure 21D:
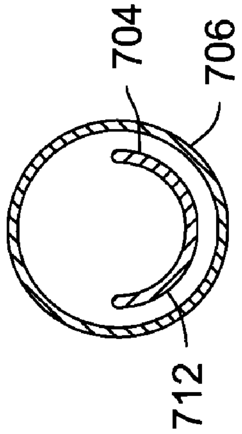
Figure 21E:
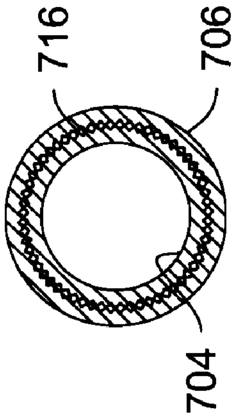

Now turning to FIG. 21D, it can be seen that just distal of the ramp shown in FIG. 21C, the outer member 706 is disposed about the skived portion 712 of the inner member 704. Preferably, the skived portion 712 of the inner member 704 extends for at least the length of a stent to be delivered such that the inner member 704 is slidable with respect to the ramp member 710 along the skived portion 712. As shown in FIG. 21E, distal of the skived portion 712 (FIGS. 21C, 21D) the inner member 704 again has a generally circular shape. If desired, the inner member 704 may be a multi-piece member having at least the skived portion comprising a hypotube member, with other portions being hypotubes, tubular polymeric pieces, or one or more polymeric pieces including braided support members. A stent 716 is shown disposed between the inner member 704 and outer member 706.

Figure 22:
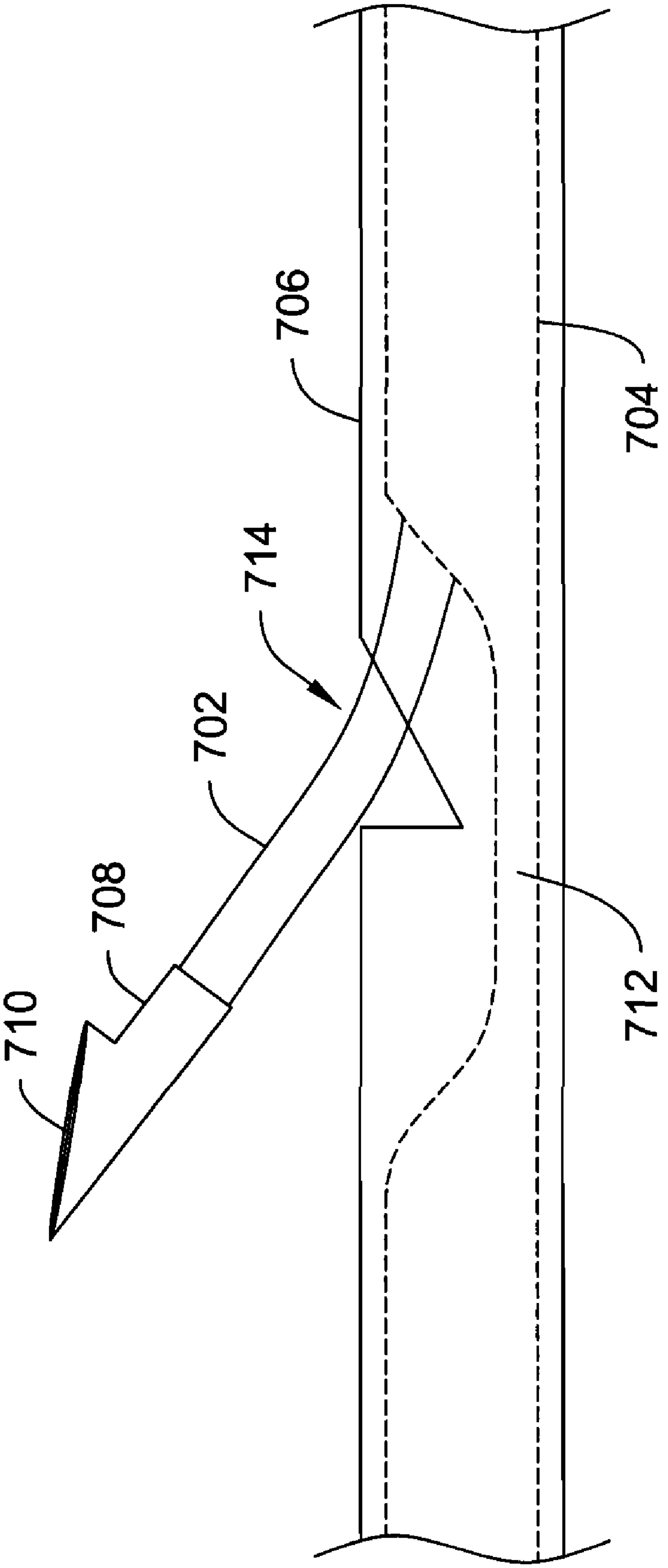
FIG. 22 illustrates a method of assembling the illustrative embodiment of FIGS. 20A-20B and 21A-21E.

FIG. 22 illustrates a method of assembling the illustrative embodiment of FIGS. 20A-20B and 21A-21E. As shown, the inner and outer members are aligned such that the skived portion 712 of the inner member 704 aligns generally with a relatively short opening 714 in the outer member 706. Next, the proximal end of the mandrel 702 is inserted and advanced in a proximal direction through the opening 714 such that the proximal end of the mandrel 702 passes into the inner member 704. The mandrel 702 is moved proximally until the ramp member 708 enters the opening 714 and the ramp 710 engages the outer member 706.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A rapid exchange type catheter adapted for placing a self-expanding stent, the catheter comprising:

an outer member having a proximal portion, a distal portion, and a guidewire port therebetween, the distal portion adapted to cover a self-expanding stent, an inner member having a proximal portion and a distal portion, the distal portion including a guidewire channel for passing a guidewire, the distal portion adapted to receive a self-expanding stent thereon, wherein the inner member is longitudinally displaceable with respect to the outer member for deploying a stent; and a mandrel member having a distal end and a proximal end, wherein the distal end has a ramp, the proximal end is coupled to the proximal portion of the outer member so as to prevent longitudinal displacement of the mandrel with respect to the outer member when the inner member is longitudinally displaced with respect to the outer member for deploying a stent.

2. The catheter of claim 1, wherein the mandrel is disposed within the outer member such that the ramp is located near the guidewire port of the outer member.

3. The catheter of claim 1, wherein the inner member, outer member, and mandrel are shaped and sized such that the mandrel and the inner member extend within the outer member.

4. The catheter of claim 3, wherein the mandrel fits within the inner member for a proximal portion of the length of the inner member.

5. The catheter of claim 3, wherein the mandrel does not fit within the proximal portion of the inner member.

6. The catheter of claim 3, wherein the mandrel and the proximal portion of the inner member lie within the outer member in a generally side-by-side fashion.

7. The catheter of claim 1, wherein the outer member is movable with respect to the inner member.

8. The catheter of claim 1, wherein the outer member and the mandrel are coupled directly.

9. The catheter of claim 1, wherein the outer member and the mandrel are coupled to by a common element.

10. The catheter of claim 1, further comprising a first proximal apparatus and a second proximal apparatus, the first proximal apparatus attached to the proximal end of the outer member and the proximal end of the mandrel, the second proximal apparatus attached to the proximal end of the inner member.

* * * * *